United States Patent [19]

Etzkorn et al.

[11] Patent Number: 5,183,936
[45] Date of Patent: Feb. 2, 1993

[54] ANHYDROUS DILUENT PROCESS FOR THE PROPYLENE OXIDATION REACTION TO ACROLEIN AND ACROLEIN OXIDATION TO ACRYLIC ACID

[75] Inventors: William G. Etzkorn, Cross Lanes; Gordon G. Harkreader, Charleston, both of W. Va.

[73] Assignee: Union Carbide Chemicals & Plastics Technology Corporation, Danbury, Conn.

[21] Appl. No.: 781,657

[22] Filed: Oct. 25, 1991

Related U.S. Application Data

[63] Continuation of Ser. No. 542,819, Jun. 25, 1990, abandoned, which is a continuation-in-part of Ser. No. 442,464, Nov. 30, 1989, abandoned, which is a continuation of Ser. No. 281,877, Dec. 8, 1988, abandoned, which is a continuation of Ser. No. 173,033, Mar. 28, 1988, abandoned, which is a continuation of Ser. No. 898,491, Aug. 21, 1986, abandoned.

[51] Int. Cl.⁵ .............................................. C07C 51/16
[52] U.S. Cl. .................................... 562/532; 562/534; 562/545; 568/476; 568/479; 568/480
[58] Field of Search ................. 562/532, 534, 545; 568/476, 479, 480

[56] References Cited

U.S. PATENT DOCUMENTS

| | | | |
|---|---|---|---|
| 3,171,859 | 3/1965 | Sennewald et al. | 260/604 |
| 3,475,488 | 10/1969 | Kurata et al. | 260/533 |
| 3,717,675 | 2/1973 | Sennewald et al. | 260/530 N |
| 3,801,634 | 4/1974 | Krabety et al. | 260/533 N |
| 4,031,135 | 6/1977 | Engelbach et al. | 260/530 N |
| 4,049,577 | 9/1977 | Childress et al. | 252/443 |
| 4,147,885 | 4/1979 | Shimizu et al. | 562/535 |
| 4,365,087 | 12/1982 | Kadowaki et al. | 562/534 |
| 4,442,308 | 4/1984 | Arntz et al. | 568/480 |
| 4,618,709 | 10/1986 | Sada et al. | 562/532 |

FOREIGN PATENT DOCUMENTS 939713 10/1963 United Kingdom ................ 562/534
2068947 8/1981 United Kingdom .

*Primary Examiner*—Arthur C. Prescott
*Attorney, Agent, or Firm*—J. F. Leightner

[57] ABSTRACT

The process for oxidation of propylene to acrolein and the oxidation of propylene to acrylic acid in two stages with acrolein as an intermediate are improved by use of essentially inert essentially anhydrous diluent gases to replace steam in the reaction streams. In particular, the use of essentially inert essentially anhydrous diluents which raise the composite heat capacity of the diluent gas mixture to at least about 6.5 calories/(gram-mole) (°C.) will improve selectively to desired products and will reduce both the waste water load on the system and by-product formation. Reduction in second-stage catalyst efficiency is compensated for by introducing steam to the feed to the second-stage, and/or by increasing the operating temperature of the second-stage, and/or by increasing the active surface area of the second-stage catalyst.

21 Claims, 2 Drawing Sheets

ANHYDROUS DILUENT PROCESS FOR THE PROPYLENE OXIDATION REACTION TO ACROLEIN AND ACROLEIN OXIDATION TO ACRYLIC ACID

This application is a continuation of prior U.S. application Ser. No. 07/542,819 filed Jun. 25, 1990, now abandoned which is a continuation-in-part of application Ser. No. 442,464 filed Nov. 30, 1989, now abandoned which is a continuation of application Ser. No. 281,877 filed Dec. 8, 1988, now abandoned which is a continuation of application Ser. No. 173,033 filed Mar. 28, 1988, now abandoned which is a continuation of application Ser. No. 898,491 filed Aug. 21, 1986, now abandoned.

BACKGROUND OF THE INVENTION

1. Field of the Invention

This invention relates to a process for the manufacture of acrolein or acrylic acid from propylene. More specifically, it describes an improved process for producing acrolein or producing acrylic acid by the catalytic vapor phase oxidation of propylene in the presence of essentially inert, essentially anhydrous diluents having specified composite heat capacity values.

2. Summary of the Prior Art

Generally, propylene in its gaseous phase is oxidized to acrolein in the presence of molecular oxygen-containing gases and steam, whose concentration is often as high as about 35 volume percent of the total feed stream, by contact at elevated temperatures with solid metal oxide catalysts. The acrolein produced in this reaction stage can be recovered or can be directed without separation of the acrolein to a second reactor operating in series with the first reactor to oxidize the acrolein to acrylic acid.

In the prior art, steam has been used in the starting reactant gas mixture in order to avoid flammable gas mixtures and because it was believed to be important to reaction selectivity, but the prior art does not recognize the importance of and unexpected effect imparted to the process of the composite heat capacity value of the gas, or steam, mixture used. For example, U.S. Pat. No. 4,147,885 relates that it is wide practice to incorporate steam to avoid burning the reactant gases and increase selectivity to acrylic acid. U.S. Pat. No. 3,475,488 discloses that it is desirable to incorporate steam in the starting reactant gas since this increases conversion and selectivity when employed in the order of 1 to 60, and preferably 5 to 30, moles of steam per mole of propylene or propylene plus acrolein.

Other patents also describe steam as the preferred diluent. For example, U.S. Pat. No. 3,171,859 states that "addition of steam is obligatory . . . it acts not only as a diluent, but also favors the reaction in that combustion to carbon oxides is substantially reduced." Also, U.S. Pat. No. 4,267,386 reiterates the general understanding among those skilled in the art, that while inert diluents may be added to the reaction system, "water, in the form of steam is desirably present . . . in amounts of from 0.5 to 15, preferably 2 to 15, moles per mole of unsaturated hydrocarbon (i.e., propylene or acrolein)." Again, with no recognition of composite heat capacity value of the diluent.

Many oxidation catalysts have been disclosed for producing acrolein in high yield by oxidizing propylene. Predominantly, these are catalysts containing mixed oxides of molybdenum, bismuth and iron with phosphorous or tungsten or antimony. Cobalt and/or nickel and alkali metals are common promoters.

Catalysts which have been found to be advantageous for use in oxidizing acrolein to acrylic acid at conversions of more than 98% generally contain mixed metal oxides. Such catalysts typically contain molybdenum, vanadium, tungsten, chromium, copper, niobium, tantalum and antimony.

The ultimate object of the teachings in the literature cited above is to obtain high performance catalysts which give high selectivities to acrolein and acrylic acid at high propylene conversions. Other factors which influence the economic viability or the improved performance of these processes are not considered in these prior art techniques. For example, they do not address the impact on process variables of use of high propylene concentrations, how to avoid the danger of explosion, the impact of inert reaction process feeds on recovery and waste disposal, or maintaining high catalyst performance over an extended catalyst life. These are all extremely important for commercial operation.

In commercial operation, it is of economic and ecological importance to minimize the presence of the steam which is fed to the reactors, since it passes through the system and becomes a burdensome waste water load after product recovery steps; nevertheless, to the knowledge of the present inventors, no commercial process has been successfully operated below a steam: propylene mole ratio of about 1.5:1. Furthermore, it is extremely important to minimize by-products which are difficult to separate from useful product or which carry a high economic penalty for disposal. Process improvements which will provide high catalyst performance while simultaneously maximizing propylene feedstock usage, and improvements which may promote conditions for extended useful catalyst life are important for commercial operation. Equally important is the ecological problem encountered when consideration has to be given to the disposal of millions of pounds of waste water, which will vary from about 0.5 to about 1.5 pounds of water per pound of acrolein/acrylic acid produced, generated by a single multimillion pound commercial facility for the production of acrolein and/or acrylic acid. The typical commercial plant has an annual capacity of from about 120 million to over 750 million pounds, thus giving an indication of the waste water problem. The prior art does not adequately address these issues.

U.S. Pat. No. 4,049,577 teaches an improved catalyst composition for making acrolein. The authors mention that recycle gas comprised of the noncondensable fraction of the product can be used in place of steam. They suggest that these recycled inerts are preferable to steam as diluent since they allow higher conversions of propylene and thus enable one to obtain higher yields, and also reduce the waste water load on the system; however, the use of recycled inerts is stated as being made possible by the characteristics of this particular catalyst composition. Nowhere does this patent suggest or teach that anhydrous diluents having hereinafter defined composite heat capacity values have an improved effect on selectivity or product mix, or are useful with other catalysts. The relationships between various diluents and the heat capacity effects on selectivity are not suggested.

U.S. Pat. No. 3,801,634 teaches the use of inert solids mixed with active catalysts in the first and second stage reactors used to manufacture acrolein and acrylic acid. The authors indicate that noncondensable, second-stage effluent gases can be recycled to the first stage as inert diluting gas which can, at least partly, replace steam. The authors do not show any relationship between the inert anhydrous diluent gases and improvements in product selectivity; or the desirable effect of composite heat capacity values.

U.S. Pat. No. 4,031,135 presents a recycle process in which noncondensable gases, preferably and generally including steam, are recycled to the first-stage reactor and also to the interstage (second-stage) reactor feed. There is no recognition of the benefits in using anhydrous diluents having certain composite heat capacity values with respect to their effect on yield, conversion, by-product selectivity mix and waste water generation. The authors do, however, recognize an apparent improved acrylic acid efficiency, which they attribute partly to the use of recycled off gas employed as the inert diluent. In column 4, lines 13-15 the patent says the off-gas "has been substantially freed from condensable products, including water, and essentially consists of nitrogen and small amounts of" other named compounds. In column 6, lines 45 to 54 the general composition, in volume percent of the off-gas is stated in broad and "especially" terms as being:

|  | broad | especially |
| --- | --- | --- |
| propylene | 0-1.5 | 0.2-1 |
| oxygen | 0-5 | 1-4 |
| CO/CO2 | 0-10 | 1-7 |
| acrolein | 0-1 | 0.1-0.5 |
| steam | 0-10 | 0.5-5 |
| others | 0-0.1 | 0.01-0.05 |
| nitrogen | 100-74 | 97.19-81.45 |

Further, in the only two examples presented in support of their invention the patentees specifically disclose the presence of 2% by volume and 8.9% by volume of steam in the recycled off-gas stream clearly not an essentially anhydrous diluent off-gas stream. The patent clearly teaches the recycle of nitrogen, in impure form, and steam in the off-gas to the reactors. In the new invention described in this specification the essentially inert diluent gas feed is an essentially anhydrous diluent gas composition, as hereinafter described. The gas feed differs significantly from the teachings of U.S. Pat. No. 4,031,135, it is essentially anhydrous. It is further to be noted that the patentees do not adequately establish improved efficiency to acrylic acid production, and that they do not recognize or disclose the effect of composite heat capacity of the diluent on product selectivities.

U.S. Pat. No. 4,365,087 refers to the recycling of dewatered residue gas, containing both inert and reactive gases, to increase the concentration of acrylic acid recovered. However, the authors not only consider this procedure unsatisfactory since the composition of the residue gas fluctuates but have no recognition of the concept of composite heat capacity of the diluent and its effect on the process.

U.S. Pat. No. 4,442,308 teaches the use of inert gases as diluent in the acrolein process; however, it specifies their use for a particular supported first-stage acrolein catalyst. Most common commercial catalysts for propylene oxidation to acrolein are neat (unsupported) and do not follow this patent's prescribed preparation. This patent also claims that 0.5 to 7 mole % steam is beneficial and its use is recommended. Nowhere in this patent do the authors teach the advantage of anhydrous diluents on product mix nor do they mention composite heat capacity or flowing heat capacity as major variables in controlling product selectivity to advantage and formation of undesired product streams.

U.S. Pat. No. 4,456,006 teaches a catalyst preparation for the propylene-to-acrolein reaction. It shows that nitrogen diluent presents an improvement over steam diluent when used with this catalyst. It does not recognize or disclose the composite heat capacity effect of diluent on product selectivity, nor does it show by-product and waste water reductions when using anhydrous diluents.

U.S. Pat. No. 3,717,675 describes a process for recovery of acrylic acid where acrolein is expelled from the aqueous acid collected and returned to the reactors to increase subsequent yields of acrylic acid. This patent mentions the use of inert diluents such as carbon oxides and nitrogen, but does nothing to demonstrate their importance. In fact, it states that it is necessary to add steam to the reaction in order to increase selectivity. This addition of steam, however, only serves to aggravate the waste water disposal problem.

UK Patent 2,068,947 teaches a process for producing methacrolein and methacrylic acid whereby inert anhydrous diluent gases are used, also combined with water vapor, to produce a product with a reduced quantity of condensables compared to the typical steam diluent process. The authors fail to recognize the relationship between anhydrous diluents and acetic acid reduction, and they do not address composite heat capacity of the diluent or selectivity improvements resultant from use of various anhydrous diluents.

U.S. Pat. No. 4,147,885 describes a recycle process in which steam is an essential ingredient. The object of the patented invention is to recycle steam to the reactors. This is contrary to the techniques of the instant invention, since it has now been found that the reduction or absence of added steam to the reactors is beneficial.

U.S. Pat. No. 4,618,709 presents an attempt to remedy, or at least alleviate, the waste water problem common to the existing catalytic oxidation processes for producing methacrolein and methacrylic acid from, e.g., isobutylene. This is accomplished in this patent by evaporating the waste water solution and subjecting the waste water vapor to combustion with molecular oxygen, whereby the amount of liquid waste water discharged is reduced. As can be seen, this is an expensive procedure since it involves two additional costly steps. In discussing the isobutylene oxidation process the patent refers to the well known and common procedure of carrying out the oxidation in the coexistence of an inert gas for dilution (column 1, lines 22-35 and 49-53) to control temperature and prevent explosion. The patent then mentions "nitrogen, water vapor, exhaust gases, etc." as examples of inert gases added and further states water vapor as being the most frequently employed, in an amount as great as 10 to 50 moles of water, or water vapor, added per mole of methacrolein or its precursor (column 1, lines 54-58). These figures clearly evidence the intentional addition of significant quantities of water to the oxidation reaction, water that becomes contaminated with reactants and products of the reaction and must subsequently be disposed of in an ecologically accepted mode. The reference nowhere suggests or discloses the importance of using an inert gas having a composite heat capacity of certain value for dilution. Nor does the reference recognize or suggest the importance of avoiding the intentional addition of supplemental quantities of water to the reaction system.

UK Patent Specification 939,713 disclosed one of the earliest catalytic processes for preparing unsaturated monocarboxylic acids from olefins. In these early processes yields of acrolein and acrylic acid were low, as evidenced by the figures presented in the examples that show low conversion, and overall yields of less than about 55% from propylene charged. By comparison, today's processes operate at exceptionally high yields, and conversions that typically approach 95% to 98%. On page 2, lines 4 to 19, this UK Specification refers to the starting materials and indicates they need not be in a pure state and may contain quantities of paraffinic hydrocarbons, such as propane or butanes. It is to be noted it is present in the starting olefin reactant as an impurity and it is not intentionally additionally introduced into the reactant as a diluent. It is also noted that its quantity is nowhere clarified and that its function is described as an entraining agent; there is no recognition of its possible use as a medium for heat removal, nor does the reference state or suggest that the hydrocarbons have any effect on maintaining the desired temperature range. Though the reference states the process can be operated in the absence of water (page 2, lines 92–94), this statement is both immediately preceded and followed by the statement that water is preferably used in quantities of from 1 to 10 moles of water, preferably 3 to 7 moles, for each mole of olefin initially introduced into the first reaction zone and all of the examples use significant amounts of water. The reference does state the reaction can be carried out in the absence of water but it nowhere indicates the water must be replaced. It merely states do not add the water. Any attempt to carry out this reaction without any added diluent would be catastrophic. In Examples I and II, 4.2 moles of water were intentionally added per mole of propylene, in Example III, 5.8 moles of water were intentionally added per mole of propylene and in Examples IV and V, 12 moles of water were added per mole of propylene. Thus, water comprised the majority of the bulk of the materials introduced in all examples. Further, nowhere in this UK Specification is there any mention of the use of any other coolant or temperature control medium. Nor is there any suggestion or recognition of the importance of the composite heat capacity of the gas diluent and its effect on conversion and yield.

None of the prior art suggests or recognizes the use of various inert anhydrous diluents in specific proportions so as to have the hereinafter defined composite heat capacity that will favorably affect the product mix obtained when using any of the commonly used catalysts.

As has been indicated above, the basic two-stage process for oxidizing propylene to acrylic acid via acrolein is well known and has been extensively described in the literature. It is also known that wet, overhead gases (noncondensables) from the acrylic acid scrubber can be recycled to the first reactor stage. By this recycling of unreacted propylene and acrolein, it is predictable that an improvement in overall yield is obtained in any chemical reaction. By use of such a recycle stream, it is also possible to provide a supplemental means of controlling the steam content to the first-stage reactor, as is taught in U.S. Pat. No. 4,147,885. In the process of that patent, the steam content of the first-stage feed is required to be 4 to 30% by volume, with all the steam, except that in the starting reactant gas mixture, being provided by the recycle stream. As discussed above, however, the presence of even as little as 4% steam is disadvantageous. This finding has not been addressed, nor even identified, by the prior art.

As has also been indicated above, nowhere in the prior art is there any disclosure or suggestion of the important role exerted on the process by the composite heat capacity of the diluent gas mixture and of the unexpected and unpredictable effect exerted by the composite heat capacity of said mixture on yield, conversion, by-product formation and waste water generation.

Application Ser. No. 886,562, filed Jul. 17, 1986, describes a process for improving the prior art processes by use of an inert diluent gas having certain composite heat capacity properties. While that process provides substantial improvements in selectivity and water load, it has been found to have the draw-back of reducing second-stage (acrolein-to-acrylic acid) catalyst activity. According to the present invention, there is provided a method for correcting that draw-back.

SUMMARY OF THE INVENTION

Figure 1:
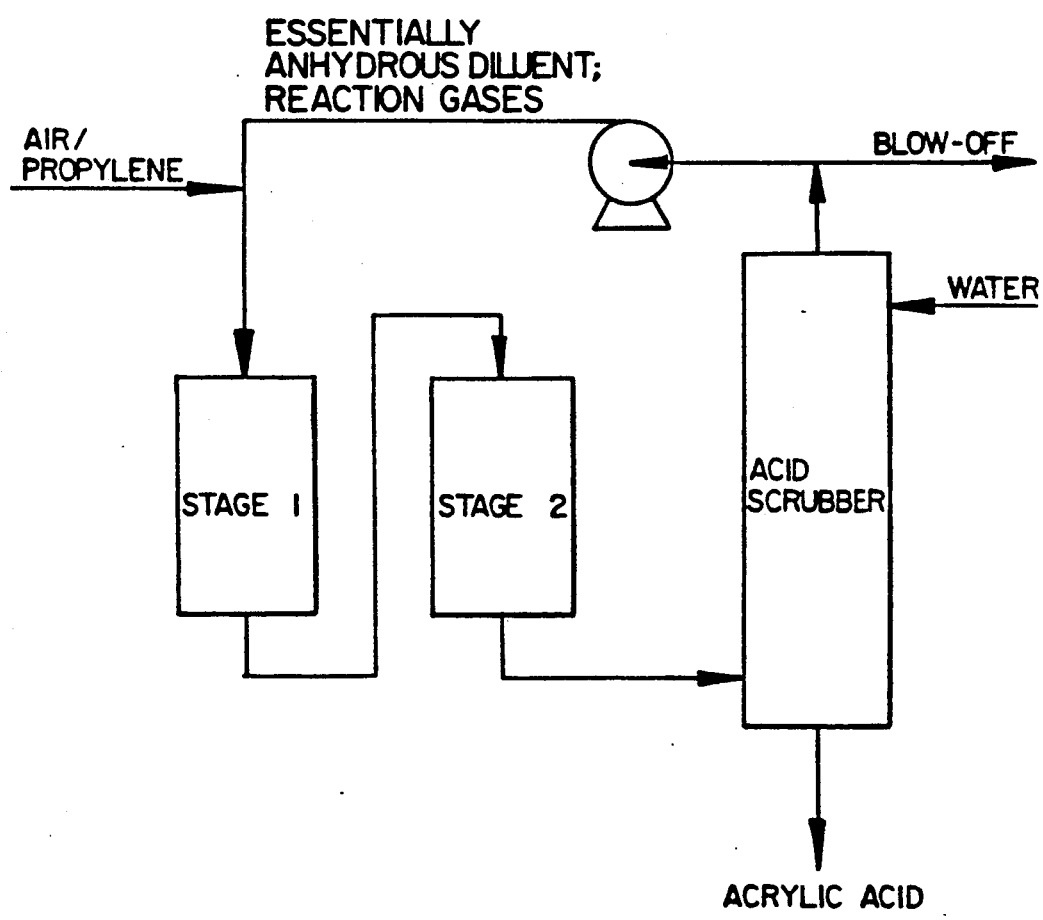
FIGS. 1 and 2 illustrate the application of recycle streams to acrolein and acrylic acid processes.

The present invention embraces two separate but related concepts, namely, the reduction by the elimination of intentionally added steam to reduce the waste water load on the process, and the improvement of selectivity to maximize the output of desired products. Both of these results are achieved by elimination of the steam diluent intentionally added in prior art processes and use of an essentially anhydrous gaseous diluent (optionally containing a minimal amount of steam which is generated from trace impurities of water that may be present in the reactants and gaseous diluents initially charged to the reactors) having a composite heat capacity in a selected range as hereinafter defined.

According to the present invention, any reduction in second-stage catalyst activity as a result of using the anhydrous gaseous diluent of this invention can be compensated for by one, or a combination of, the following: (a) increasing the operating temperature of the second-stage catalyst bed by about 5°–10° C., (b) increasing the surface area of the second-stage catalyst, and/or (c) adding a limited amount of steam to the second-stage feed (inlet) stream as hereinafter defined.

In a preferred embodiment, a portion of the non-condensable essentially anhydrous gases from the process, e.g., the overhead stream from the acrylic acid scrubber, is recycled back to the first-stage reactor feed stream. In addition, most preferred would be the use of enriched or pure oxygen in the two stages to replace the use of air.

It will be understood that the process of this invention can be applied not only to a combined propylene-acrolein-acrylic acid process, but also to a separate acrolein-acrylic acid process, or to the acrolein-acrylic acid leg of a propylene-acrylic acid process. Thus, a portion of the product stream from the first-stage propylene-acrolein reactor can be sent to an acrolein recovery process, from which some or all of the non-condensable overhead gases from the acrolein scrubber system can be recycled as diluent to the first and/or second-stage of the propylene-acrylic acid process.

DESCRIPTION OF THE INVENTION

According to the invention, it has been discovered that essentially anhydrous diluent gases having high heat capacity can be used in the propylene oxidation reaction to efficiently produce acrolein and acrylic acid. (For purposes of this invention, a diluent is any gas which does not react in the reaction stage in which it exists.) Furthermore, when using essentially anhydrous diluents, the formation of two major by-products, acetaldehyde and acetic acid, is significantly reduced. This reduction in by-products is especially important since acetaldehyde is difficult to separate from acrolein in recovery operations, and therefore causes an economic penalty in the refining of the product for sale. Likewise, acetic acid and acrylic acid are difficult to separate from each other. To make saleable quality acrylic acid, considerable energy is required to more completely remove the acetic acid. Furthermore, the acetic acid separation step causes acrylic acid recovery losses, and waste disposal costs for disposing of acetic acid are high. The present invention provides a means for reducing the waste water load, reducing acetic acid disposal costs, decreasing separation costs for both acrolein recovery and acrylic acid recovery, and enables existing equipment to enact a better separation, thus reducing acrylic acid losses and providing potential for higher quality refined product.

Another key discovery of this invention is that by increasing the flowing heat capacity of the reactant gas mixture, the yield of useful products can be increased significantly. The flowing heat capacity is increased by the introduction of an essentially anhydrous diluent having a relatively high composite heat capacity (as defined herein), comprising one or more essentially inert essentially anhydrous gases with relatively high molar heat capacities. Flowing heat capacity is the composite heat capacity of the essentially anhydrous diluent plus the heat capacity of the reactants, i.e., the flowing heat capacity is the composite heat capacity of the total gas stream. However, flowing heat capacity does not change appreciably as a result of reaction, since various reaction products have a higher heat capacity than that of the reactants, and some have a lower heat capacity. In general, the flowing heat capacity will not be expected to typically change by more than about one heat capacity unit as a result of reactions. Thus, the composite heat capacity of the diluent is a dominant variable for process control purposes.

As the flowing heat capacity of the reaction feed gas mixture is increased, yield to acrolein, and acrolein plus acrylic acid increases, and the flammable gas range is reduced, enabling higher productivity operations. Simultaneously, the peak temperature in the catalyst bed due to the exothermic heat of reaction is lessened and the heat of reaction that is released is absorbed more efficiently in the bulk gas stream. This, in turn, should increase catalyst life by decreasing thermal stresses within the catalyst pellets' structure, reducing potential carbon build-up within catalyst pores, and by reducing pressure drop, since there will be lower volumetric flow of reactant gas feeds necessary to meet a given production level.

The invention is advantageous for recycling diluent gases and unreacted propylene back to the reactors. The resulting low-steam-containing product streams provide an ample source of noncondensable diluent, so that separation of useful product is simplified. This is particularly advantageous for acrolein recovery, since acrolein, which is more volatile than water, can be effectively separated from the reaction-produced water without loss of diluent. By using essentially anhydrous diluents with higher volatilities compared to acrolein, the present invention permits operation on an acrolein recovery system with recycle of diluent, unreacted propylene, and unrecovered acrolein back to the reactor for further efficiency gains and cost reductions. Such a system using steam diluent is not possible when adapting prior art acrolein recovery equipment and techniques. It also enables implementation of recycle processes in which components such as acetic acid and acrylic acid and other minor, heavy by-products are excluded from the recycle stream. This is significant since the acids and heavy by-products are suspected of adversely affecting catalyst life, and furthermore, it aids in minimizing recycle handling problems, such as compressor corrosion.

The composition of the process feeds must be comprised so that flammable gas mixtures are not formed. According to this invention, the starting reactant gas mixture to the first-stage reactor typically contains up to about 16 g-moles per hour of propylene, preferably up to about 10 g-moles of propylene, per liter of first-stage catalyst; about 1.1 to about 2.1 moles of molecular oxygen per mole of propylene, and an essentially inert essentially anhydrous diluent gas having a composite heat capacity of at least about 6.5 calories/gram-mole (°C.) which comprises about 40 to about 94% by volume of the feed stream. The oxygen source can be air, oxygen-enriched air, essentially pure oxygen or a mixture of oxygen and essentially inert anhydrous gases. As used in this specification by the term essentially inert essentially anhydrous diluent gas (or variant thereof) is meant the inert gas stream of one or more gases introduced into a reactor to which additional water in any form has not intentionally been added before the inert gas is introduced into the reactor but which inert gas stream may contain trace impurities of water, or which water may have been introduced into the reactor as a trace impurity present in the oxygen feed, or formed during the reaction. It is desirable that the mole ratio of composite diluent to propylene be in the range of about 2 to about 32. The essentially anhydrous diluent gas typically comprises a mixture of nitrogen, carbon dioxide, methane, ethane and propane; however, any other essentially anhydrous inert gas can be included. Some other useful inert gases include helium, argon, hydrogen, saturated hydrocarbon gases, $N_2O$, and carbon monoxide. When water is present as a trace impurity in any of the materials introduced into the reactors, at the elevated temperature required for these reactions the water is immediately converted to steam. The materials used should preferably be free of any water, but in those instances in which water may be present as an impurity, the total amount thereof in all materials added should be no more than about 0.4 mole per mole of propylene, preferably less than about 0.3 mole per mole of propylene and most preferably zero. The inert diluent should be of sufficient quantity to avoid flammable mixtures when combined with the propylene and molecular oxygen. Air or an oxygen enriched stream or pure oxygen can be used as the molecular oxygen source. Of course, if air is used, the contained nitrogen acts as a supplemental diluent. In the process of this invention the intentional introduction of extraneous steam to a reactor is not contemplated.

For each essentially inert essentially anhydrous diluent gas mixture there is a relationship which can be determined by experiment and which describes the limiting compositions of oxygen, propylene, and inert diluent gas for which flammable mixtures exist. Most commercial applications will be operated in a "fuel-rich" mode, whereby the oxygen content is the limiting factor from a flammability standpoint. The propylene concentrations will be determined by catalyst performance and by commercial cost effectiveness factors.

It is a distinct advantage of this invention that, since diluent gas mixtures with high composite heat capacities have a tendency to broaden the operable range due to shrinkage of the flammable gas envelope, high propylene concentrations are possible. It is theorized that first-stage propylene feed concentrations as high as about 30 mole % will be achievable using the method of this invention.

Typically approximate ranges for feed compositions are defined based on the generalized operating constraints discussed above. First-stage feeds in the following quantities are typically particularly useful:

Propylene: Up to about 16 g-mole per hour/liter of first-stage catalyst, preferably up to about 10 g-mole per hour/liter of first-stage catalyst;

Oxygen: 1.1 to 2.1:1 $O_2/C_3H_6$ ratio, such that there is up to about 33.6 g-mole per hour $O_2$/liter of first-stage catalyst, preferably up to about 21 g-mole per hour $O_2$/liter of first-stage catalyst;

Diluent: About 2 to 32:1 inert diluent/$C_3H_6$ ratio, preferably 3.5 to 12:1 inert diluent/$C_3H_6$ ratio. Nevertheless, one can use amounts slightly below or slightly above the above ratios, e.g., one can go as low as about 0.5:1 and as high as about 33:1.

The process of the invention is particularly advantageous in that it is not dependent upon any particular catalyst, as is much of the prior art, and will provide its benefits for any catalyst of choice. Any molybdenum, bismuth, iron-based mixed metal oxide oxidation catalyst, such as those disclosed in U.S. Pat. Nos. 3,825,600; 3,649,930, and 4,339,355, can be used in the propylene-to-acrolein oxidation reactor. A Mo, V-based mixed metal oxide oxidation catalyst (such as described in U.S. Pat. Nos. 3,775,474; 3,954,855; 3,893,951; 4,339,355) can be used effectively in the second-stage of the propylene oxidation to acrylic acid (i.e. the acrolein oxidation to acrylic acid reaction).

The general reaction conditions are not narrowly critical, and are those known to the art. The first-stage reaction operates at temperatures of 250° C. to about 450° C., although temperatures of about 300° C. to about 400° C. are preferred. The second-stage reaction, according to the prior art, requires temperatures of about 200° C. to about 450° C., with a preferred temperature of about 250° C. to about 375° C. According to the present invention, however, those temperatures should, as one option, be raised about 5° to 10° C.

Operating pressures of about 1 to about 4 atmospheres are typical, although this process improvement will apply for all operating pressures, whether subatmospheric, atmospheric, or superatmospheric. Preferred commercial modes of operation will minimize pressures, but pressures are typically held in the 2 to 3 atmosphere range due to system pressure-drop constraints.

Flow rates can be varied from about 0.5 to about 15 seconds contact time; however, typical commercial flow provides about 1.5 to about 4 seconds contact time. Contact times of about 1.7 to about 3 seconds are preferred.

As indicated above, selection of proper composite heat capacity of the essentially inert essentially anhydrous diluent gas or gases is critical to the proper performance of the invention. Since the essentially inert essentially anhydrous diluent gas stream may comprise a mixture of several individual gases, it is convenient to refer to a composite heat capacity for the total stream. The term "composite heat capacity," as used herein, means the sum of the products of the volumetric fraction of each gas in the diluent gas mixture and its heat capacity. (Heat capacity, as referred to herein, is the ideal gas heat capacity determined at 330° C. for purposes of the composite heat capacity definition.) The composite heat capacity for the essentially inert anhydrous diluent gas going to the first-stage reactor should be at least about 6.5 calories/gram-mole (°C.). Below this value, the product selectivity benefits of this invention are minimal. There is no known upper limit on composite heat capacity; however, it is theorized that above a value of about 40 there may be an unrecoverable heat loss through absorption of reaction heat into the process stream, which would result in an economic penalty. In addition, there could be a problem with increased after-burning at the exit of the first-stage reactor. It is preferred that the composite heat capacity be maintained from about 8 to 20, and most preferably about 10 to 17. Assume the presence of four gases in the inert gas stream, A, B, C, D, in volumetric presence of 20% A, 40% B, 30% C, 10% D. Assuming heat capacity in degrees centigrade of w cal/gram-mole for gas A, x cal/gram-mole for gas B, y cal/gram-mole for gas C and z cal/gram-mole for gas D. Then the "composite heat capacity" (CHC) of the inert diluent gas stream is expressed by the equation:

$$CHC = (0.20)(w) + (0.40)(x) + (0.30)(y) + (0.10)(z)$$

The sum of these should be at least about 6.5 calories/gram-mole (°C.) as indicated above.

The flowing heat capacity of the second-stage reactor feed gases is determined predominantly by the choice of essentially inert anhydrous diluent gas fed to the first-stage reactor. The first-stage product mix has only a minor influence on the second-stage feed flowing heat capacity, since the products typically account for only about ten to twenty percent of the total stream volume. For example, a typical operation with 7% propylene and 13% oxygen produces water plus acrolein, acrylic acid, acetaldehyde, acetic acid, and carbon oxides. The average heat capacity of the feed propylene and oxygen is very nearly the same as the average heat capacity of the resulting products (approximately 0.65 cal/g-mole (0° C.) more for products versus reactants).

The essentially inert anhydrous diluent gas of this invention introduced into the reactor can be a single gas or a multi-component mixture of gases, provided that certain criteria are observed. Each gas must be essentially inert to the oxidation reactions of the process, and each gas must be non-condensable under typical operating conditions and readily separable from the reaction products.

Since each plant installation will have specific constraints that affect the energy usage for the entire plant, attention must be paid to the impact on the plant energy balance for use of particular diluents which alter the current heat recovery schemes. For example, a high heat capacity diluent will retain more of the heat evolved through reaction, whereas now the bath temperature is relied on more to remove and recover the heat of reaction. High heat capacity diluents will require more attention to recovering heat after the reaction. Furthermore, if process off-gas is disposed of via combustion, the recovery of heat will be affected by a major change in diluents.

In addition, one should avoid catalyst poisons, e.g., sulfur dioxide, and gases that react to form unwanted by-products, as would $C_4$-unsaturated compounds; or $NH_3$, which produces acrylonitrile.

It is another advantage of this invention that the steam component typically intentionally introduced with the feed to the first-stage can be minimized, even eliminated. While there is controversy among those skilled in the art as to the precise function of steam, e.g., whether it is truly an inert diluent or whether it somehow participates in the oxidation of propylene and acrolein, it is accepted practice in the art as it is currently performed that a significant concentration of steam is required in order to successfully operate the first-stage and second-stage reactions. Contrary to this holding of the art, it was a surprising, unexpected and unpredictable discovery of the present invention that intentional addition of steam is desirably eliminated entirely. This is accomplished by substituting for the steam the essentially inert essentially anhydrous gas diluent of selected composite heat capacity as described this invention. Accordingly, it has been found that the steam content of the feed gas can be essentially zero. While not preferred, the steam content of the feed gas may range as high as about 3% by volume of the feed gas when the materials comprising the feed gas have not Previously been treated to remove water. However, it is preferred that the steam content resulting from water as an impurity in the feed stream be kept below about 2%, more preferably below about 1%, by volume and most preferable zero. Since steam is not intentionally added to the reactors the waste water disposal problem is significantly reduced.

As indicated above, it has been observed that in the second-stage (acrolein-to acrylic acid reaction step), the replacement of a substantial amount of steam with essentially anhydrous diluent can reduce the activity of the second-stage oxidation catalyst. According to the present invention, it has been found that second-stage catalyst activity can be restored by increasing the operating temperature of the second-stage by about 5° to 10° C., preferably abut 10° C., above that required if the second-stage inlet stream contained about 45 mole percent steam.

According to the present invention, it has also been found that second-stage catalyst activity can be restored by introducing steam to the second-stage, such that the steam content is preferably no more than about 45 mole percent of the inlet stream to the second-stage. When introducing steam to the second-stage reactor, the steam content of the inlet stream should be adjusted to no more than about 45 mole percent of the inert gas components of the stream. Most preferably, the steam content will be no more than about 20 mole percent of the inlet gas stream introduced to the second-stage reactor.

Additionally, according to the present invention it has further been found that a reduction in second-stage catalyst activity can be corrected by increasing the available surface area of the second-stage catalyst sufficiently to compensate for the observed loss of catalyst efficiency. Such increase in catalyst surface area can be accomplished by utilizing smaller catalyst pellet size, or more efficient shape, or by increasing the length of the catalyst bed.

While not an absolute requirement of this invention, it is highly preferred that the essentially inert anhydrous diluent gas used be, at least in part, an essentially anhydrous recycle stream from within the process. Preferably, this will comprise a portion of the non-condensable, overhead gas mixture from the acrolein or acrylic acid recovery scrubber train which removes water and acrylic acid from the product mixture. In particular, the use of low-boiling, anhydrous diluents makes recycle from an acrolein recovery process possible. Besides providing a beneficial system which allows recovery of current acrolein separation efficiency losses and reuse of unconverted propylene, recycling process gases from an acrolein recovery process is desirable and advantageous to recycling process gases from an acrylic acid recovery process as described in the prior art. Generally, in the process of this invention, additional high heat capacity inert diluent is added to the recycle stream.

In order to minimize the water vapor carried overhead from these scrubbers, they should be operated within the ranges of conditions shown in Table A.

TABLE A

|  | ACRYLIC ACID SCRUBBER: (Acrolein Recovery System Or Acrylic Acid Recovery System | ACROLEIN SCRUBBER: (Acrolein Recovery System) |
|---|---|---|
| BASE TEMP. (°C.) | <95, preferably: <80 | <45, pref.: 15 to 35 |
| HEAD TEMP. (°C.) | <80, pref.: <70 most pref.: <60 | <40, pref.: 10 to 30 |
| PRESSURE (ATM) | <3, pref. 1 to 2 | <3, pref.: 1 to 2 |
| SCRUBBING MEDIUM FLOW (Volume) BOTTOM PRODUCT STREAM FLOW (Volume) | <1:1 pref.: <1:2. |  |
| SCRUBBING MEDIUM FLOW (Weight) ACROLEIN BOTTOMS FLOW (Weight) |  | <80:1 pref.: <30:1 |

Under most operating conditions, it will be necessary to take off a purge stream, the size and location of which will be determined by the specific process being used. If pure oxygen is used as the source of oxygen, the purge can be relatively small. If air is used as the oxygen source, there will be a build-up of inerts, e.g., nitrogen, so that a substantial purge will be required, and will be controlled to maintain the desired composite heat capacity. The use of pure oxygen (i.e., oxygen not burdened with substantial concentrations of inert gases) permits maximization of diluents with a heat capacity higher than that of nitrogen. This permits minimization of the purge, which in turn, makes feasible the use of high heat capacity inert gases, such as propane, which might be too expensive for use as inert diluents if they were to be substantially lost through purging.

In the examples below, various anhydrous and aqueous diluents were examined in a pilot-scale reactor system consisting of two single tubular reaction vessels of typical commercial reactor tube dimensions. The first reactor tube contained a commercial catalyst comprising molybdenum, bismuth, iron and several promoter metals typical of first-stage catalyst, as described above. The second reactor tube was filled with a commercial second-stage catalyst, similar to those described previously, and was connected in series with the first. The gaseous reaction products were sampled and separated into condensable and noncondensable portions. Each phase sample was measured and analyzed by gas chromatograph. The resultant measurements were used to calculate reaction yields and propylene conversions. These sampling procedures were accomplished for both first-stage product and second-stage product, so that process performance for acrolein production and process performance for acrylic acid production were both determined.

The experiments summarized in Table I were set up in a statistical design, and the same statistical design was used for several diluents. These diluents included nitrogen, carbon dioxide, methane, propane and steam (for comparative purposes).

Additional investigations summarized in Table II included a statistically designed set of experiments in which the composite heat capacity of the diluent gases was varied systematically to illustrate the effect of the composite heat capacity on overall performance.

In addition, a series of recycle runs in which fresh air and propylene were fed to the reactors along with a diluent gas stream obtained by recycling a portion of the uncondensable product stream from the second-stage reactor was carried out (Ex. 8).

In all the designed experiment sets, the prototype reaction feed concentrations of 7.0 mole % propylene, 60.2 mole % air, and 32.6 mole % diluent were used. The diluent consisted of (i) steam or (ii) steam plus inert anhydrous diluent or (iii) essentially inert anhydrous diluent. The steam-to-anhydrous diluent additive ratio was varied as discussed in the design below.

The experiments were run in a $2^3$- factorial design with four center points. The independent variables were first-stage temperature, space velocity, and steam feed concentration. The propylene feed concentration (7 mole %) and air-to-propylene feed concentration ratio (8.6) were fixed, as were the system pressure and second-stage operating conditions. The major objective of the experimental set-up was to describe the first-stage (acrolein) catalyst performance with various concentrations of inert anhydrous diluent and steam. The designed set of experiments is outlined below.

| | + | Center Point | − |
|---|---|---|---|
| space velocity (hr$^{-1}$) | 2000 | 1600 | 1200 |
| temperature (°C.) | 340 | 330 | 320 |
| steam conc. (mole %) | 30 | 20 | 10 |
| (inferred anhydrous diluent conc. (mole %)) | 2.6 | 12.6 | 22.6 |

By the term "inferred" is meant the diluent gas added to the air, propylene, and steam mixture. This number does not take into account the nitrogen diluent inherent in the air feed.

In addition to the basic designed set of experiments, two 0% steam runs were run at outlying points of the experimental space. A composition profile run was made at 0% steam and 160 hr$^{-1}$ space velocity. Several additional tests were made to verify hotspot temperature observations. Linear regression models that gave the best-line-fit with minimal residual variance were developed. The t-ratio for each contributing independent variable had at least a 95% confidence limit on its significance, based on standard statistics calculations. Most variables had a 99% confidence limit if included in the model equations. In general, the equations provided a very good fit to the data.

The terms "conversion," "yield," "selectivity," "space velocity," and "contact time" are defined as follows:

$$\text{conversion \%} = \frac{\text{moles propylene converted}}{\text{moles propylene fed}} \times 100$$

$$\text{yield (mole \%)} = \frac{\text{moles product produced}}{\text{moles propylene fed}} \times \frac{\text{number carbon atoms in product}}{3} \times 100$$

$$\text{selectivity (mole \%)} b = \frac{\text{moles product produced}}{\text{moles propylene converted}} \times \frac{\text{number carbon atoms in product}}{3} \times 100$$

$$\text{space velocity (hr}^{-1}) = \frac{\text{gas volumetric flowrate (1/hr)*}}{\text{volume of reactor catalyst bed (1)}}$$

$$\text{contact time (seconds)} = \frac{3600}{\text{space velocity}}$$

*Flow adjusted to standard temperature and pressure (i.e., 0° C. and 1 atm).

EXAMPLES

The examples which follow illustrate and explain the invention, but are not intended to limit it in any way. In these examples, all concentrations are in mole percent.

Example 1

This example shows the unexpected advantages achieved by the inert anhydrous diluent process of this invention (Part D) compared to processes in which steam is intentionally introduced into the reactor (Parts A, B, C). The intentional introduction of steam is the mode in which all existing propylene oxidation plants of this nature currently operate. As shown by the data in Table I the total acetic acid plus acetaldehyde yield decreased to about one-half to two thirds of the amount formed when steam is intentionally introduced. A further advantage, not shown in the table, is the fact that the absence of added steam decreases the waste water load and eliminates the costs associated with treatment of the waste water prior to disposal.

Part A—The experimental set-up for the pilot plant reactor tubes was as described above. It consisted of two like tubular reactors, each consisting of one tube filled with an appropriate catalyst, as described above. A jacket surrounding each tube was filled with a heat transfer fluid which circulated to remove heat of reaction. Thermocouple and sample taps were provided along the length of each reactor and at the bottom of each reactor. Gas feeds were metered into the first reactor using mass flowmeters. The first-stage effluent was then conducted directly into the second-stage reactor. The condensable portion of the second-stage effluent was recovered as a liquid tails stream from a water-based scrubber. Non-condensable gases were conducted out the top of the scrubber, and could be returned, if desired, to the reactors to supply additional diluent gas. The system outlet pressure was controlled at 7 psig in order to control reactor feed pressures on the system. Propylene feed concentration was set at 7.0% and air feed concentration was set at 60.2 %. The additional (to nitrogen in the air feed) feed gas diluent contained 2.6% nitrogen and 30% steam. (Also present was about 0.2% inert impurities in the propylene.) The system outlet pressure was set at 7 psig, and reactor temperature was adjusted to 320° C.

Part B—Part A was repeated, but the additional diluent feed contained 12.6% nitrogen and 20% steam.

Part C—Part A was repeated, but the diluent feed was 22.6% nitrogen and 10% steam.

Part D—Part A was repeated, but with 32.6% nitrogen and 0% steam as the diluent gas. Temperature was adjusted to give a first-stage propylene conversion of 94.5%.

The results are shown in Table I; also shown are the composite heat capacity (CHC) values of the inert diluent feeds.

Example 2

The conditions of Example 1 Parts A through D were repeated with methane instead of nitrogen in the diluent gas, the remainder being steam.

The above examples of the first-stage catalyst performance clearly demonstrate that as the steam feed concentration decreases (descending order for Examples 1 and 2), that the total acetaldehyde plus acetic acid yield also decreases. This decrease is then directly translated to the second-stage reaction in the overall determination of acetic acid yield. Furthermore, in directly comparing Examples 1 and 2, it is evident that acrolein plus acrylic acid yield is significantly higher for the methane (higher heat capacity), compared to nitrogen, diluent. Again, these yields translate directly to the overall two-stage acrylic acid yield.

Over the range of these experiments, each percentage point increase of steam intentionally introduced in the feed to the first stage provides a increase in the acetaldehyde-plus-acetic acid yield above the 0% steam level. This is shown in the following relationship:

$$\text{Acetaldehyde + Acetic Acid Yields} = 1.7535 + 0.0304(\text{mole \% steam} - 20)$$

TABLE I

| | | | | | | | | | Mole % Yields | |
|---|---|---|---|---|---|---|---|---|---|---|
| | Mole % $CH_4$ | Mole % $N_2$ | Mole % $H_2O$ | (f) CHC | $SV^{(a)}$ $(hr^{-1})$ | (°C.) $T_1^{(b)}$ | (°C.) $T_{1-HOT}^{(c)}$ | % $C_3$ $Conv.^{(d)}$ | Acrolein | Acrylic Acid | HAc + $HOAc^{(e)}$ |
| Example 1 | | | | | | | | | | | |
| Part A | — | 2.6 | 29.5 | 7.9 | 1985.2 | 320.1 | 388.9 | 93.3 | 77.1 | 10.4 | 1.95 |
| Part B | — | 12.6 | 19.92 | 7.73 | 1689.6 | 329.2 | 393.4 | 96.99 | 77.97 | 13.35 | 1.84 |
| Part C | — | 22.6 | 10.16 | 7.55 | 1994.2 | 320.4 | 398.3 | 94.85 | 76.9 | 11.9 | 1.57 |
| Part D | — | 32.6 | 0 | 7.37 | 1585.1 | 314.5 | 397.3 | 94.48 | 81.97 | 6.97 | 1.01 |
| Example 2 | | | | | | | | | | | |
| Part A | 2.6 | — | 29.51 | 8.07 | 1931.4 | 320.8 | 389.0 | 95.06 | 80.17 | 9.67 | 1.85 |
| Part B | 12.6 | — | 20.55 | 8.56 | 1611.8 | 330.3 | 394.2 | 97.32 | 79.5 | 12.3 | 1.66 |
| Part C | 22.6 | — | 10.74 | 9.05 | 1989.3 | 319.9 | 400.1 | 95.92 | 79.32 | 10.98 | 1.47 |
| Part D | 32.6 | — | 0 | 9.54 | 1562.2 | 324.4 | 387.8 | 95.7 | 80.4 | 10.8 | 0.68 |

$(a)$Space Velocity
$(b)$First-stage reactor bath temperature
$(c)$First-stage reactor peak catalyst temperature
$(d)$Propylene Conversion
$(e)$Acetic Acid + Acetaldehyde
$(f)$Composite heat capacity, cal/g mole (°C.), based on ideal gas heat capacities at 330° C.

Experiment A

The experimental set-up for Examples 1 and 2 was duplicated; however, the only diluent used was steam, i.e., the feed consisted of 60.2% air, 7.0% propylene, and 32.6% steam. This is typical of the conventional feed composition employed in the first-stage of the process is currently practiced commercially and as it is described in the prior art, this experiment is presented for use as a comparison to the first-stage performance data of Examples 3 through 7.

Example 3

The experimental set-up used in Examples 1 and 2 was repeated. Propylene feed concentration was set at 7.0% with air as the molecular oxygen-containing gas in the amount of 60.2% of the reactor feed stream. The remaining feed was comprised of essentially inert anhydrous diluent gas made up of propane and nitrogen. The quantities of nitrogen and propane were adjusted so that the combined essentially inert anhydrous diluent gas mixture had the same composite heat capacity as found with steam alone. Steam was not introduced. This amounted to 6.4% propane and 26.2% nitrogen in the reactor feed gas stream. System outlet pressure was controlled at 7 psig, and reactor temperature was maintained at 330° C.

Example 4

Example 3 conditions were duplicated with the exception that the essentially inert anhydrous diluent gas feed was comprised so that it had the same average composite heat capacity as methane. However, steam was not introduced. Propane diluent concentration was 2.0% and nitrogen diluent concentration was 30.6% of the reactant feed mixture.

Example 5

The conditions of Example 4 were repeated with an essentially inert anhydrous diluent gas feed having a propane concentration of 10.8% and a nitrogen concentration of 21.8%.

Example 6

The conditions of Example 4 were repeated with an essentially inert anhydrous diluent gas feed having a propane concentration of 23.0% and a nitrogen concentration of 9.6%.

Example 7

In this example, the propylene feed and air feed flow rates were set identical to the conditions used in Examples 3 through 6. In this case, the volumetric flow of essentially inert anhydrous diluent gas was lowered, but the composite heat capacity of this essentially inert anhydrous diluent was the same as that of essentially inert anhydrous diluent used in Example 5. This was done by running the following feed conditions: 1380 $hr^{-1}$ space velocity, 8.33% propylene, 69.8% air, 14.6% nitrogen, and 7.26% propane.

The results obtained in Experiment A and Examples 3 to 7 are set forth in Table II.

By comparing the acrolein plus acrylic acid yield in Experiment A to the yields obtained in Examples 4 through 7, it is clear that higher heat capacity generally provides higher efficiency to useful products. Furthermore, as shown in the data, the absence of steam diluent in Examples 3 to 7 results in a dramatic reduction in unwanted by-products acetaldehyde plus acetic acid. Thus, in Experiment A (the prior art conventional aqueous steam diluent process) the total yield of acetaldehyde plus acetic acid was 1.8%; in Examples 3, 4 5, 6 and 7 it was, respectively, 0.94%, 1.06%, 1%, 1.04% and 1.09%. This is equal to a significant decrease of from about 40% to about 50% of these undesired by-products. That such a dramatic reduction would result in the absence of aqueous diluent could not be predicted. Example 7 also shows that by using essentially inert anhydrous diluents with high composite heat capacity, the process can be run using lower volumetric flow rates of diluent while maintaining high yields of useful products. These results were completely unexpected and could not be predicted from the prior art.

Over the range of the experiments of Examples 4 to 7, with composite heat capacities in the 7 to 14.1 range, the following relationships represent the expected trends in useful product yields:

(a) Acrolein yield = 1.224(CHC) + 69.3084
(b) Acrolein & Acrylic acid yield = 0.756(CHC) + 83.7744 where CHC = diluent composite heat capacity, as defined above.

improve reaction efficiencies and process economics. More specifically, recycling of product or a portion of a product stream enables efficient use of feed material not reacted in a single pass or reuse of feed material which is costly to make up in the reactor feed stream. Use of essentially anhydrous inert diluents has a particularly advantageous effect on the operability of recycle. It enables using a recycle stream which has less acid, thus increasing compressor operability. Furthermore, prior art recycle processes require more elaborate sampling mechanisms in order to reliably measure recycled oxygen concentrations. The control of oxygen is essential to safe operation of these recycle processes due to concerns over flammable gas mixtures. The essentially anhydrous streams of this invention, however, provide for reliable and accurate monitoring of oxygen, thereby increasing the recycle process reliability and operability as well as safety.

Figure 2:
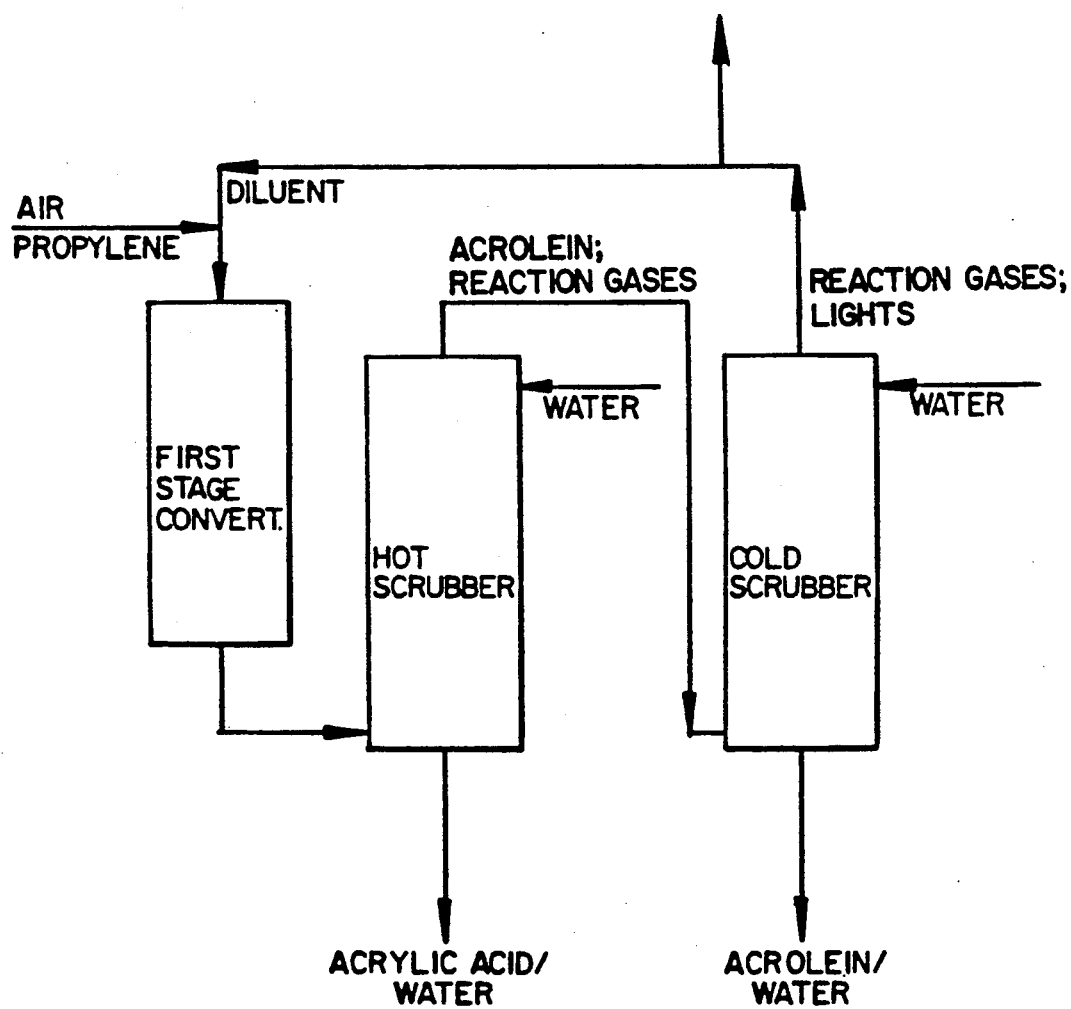

Furthermore, an essentially anhydrous inert diluent process allows simple, efficient recovery and recycle of acrolein in an acrolein production unit. FIGS. 1 and 2 illustrate the application of recycle to the acrolein and acrylic acid processes.

Example 8 (recycle)

The product gas from the second-stage reactor was condensed to remove all condensable components including any water formed during the reaction. A portion of non-condensed components of this product stream containing nitrogen, carbon dioxide, carbon monoxide, oxygen, and propylene was directed to a compressor and compressed up to approximately 30 psig for recycle and feed to the reactors. The quantities of oxygen and propylene coming over in this recycle stream were calculated, and make-up propylene and air were added so that the reactor feed stream contained 7.0% propylene and 12.6% oxygen. The temperature of the first-stage reactor was controlled so that propylene conversion was 95%. The second-stage temperature was likewise controlled so that acrolein conversion was more than 99%. The first-stage acrolein yield was measured at 78% and the first-stage acrylic acid yield measured at 12.2%. The overall (two-stage) yield to acrylic acid averaged 85%. The absence of steam in the initial feed of inert diluents resulted in a significant decrease in the waste water load; this was true for all of the above examples.

Experiment B

The experimental set-up for Experiment A was essentially duplicated. In this experiment the reaction was carried through the two-stages and the data is presented to show the effect of increasing temperature of the second-stage of the process. The experiment was per-

TABLE II

| | (Cal/g-mol(°C.)) | | | FIRST-STAGE PERFORMANCE | | | % Yld. to: | | | | | |
|---|---|---|---|---|---|---|---|---|---|---|---|---|
| Diluent | CHC | SV | $T_1$ | % $C_3$ Conv. | $CO_2$ | CO | HAc | ACR | HOAc | AA | AA + ACR |
| Steam (Exp. A) | 7.95 | 1600 | 325 | 95.6 | 2.3 | 1.5 | 1.20 | 77.9 | 0.6 | 11.5 | 89.4 |
| $C_3H_8/N_2$ (Ex. 3) | 7.95 | 1600 | 320 | 95.02 | 2.89 | 1.61 | .63 | 79.57 | .31 | 9.75 | 89.31 |
| $C_3H_8/N_2$ (Ex. 4) | 9.25 | 1600 | 330 | 96.61 | 3.39 | 2.06 | .63 | 76.3 | .43 | 13.6 | 89.9 |
| $C_3H_8/N_2$ (Ex. 5) | 10.55 | 1600 | 320 | 96.65 | 1.84 | 1.25 | 0.71 | 82.91 | .29 | 10.4 | 93.29 |
| $C_3H_8/N_2$ (Ex. 6) | 14.13 | 1600 | 320 | 98.31 | 1.85 | .967 | 0.72 | 86.65 | .32 | 7.31 | 93.96 |
| $C_3H_8/N_2$ (Ex. 7) | 9.59 | 1380 | 320 | 96.66 | 3.15 | 1.72 | 0.73 | 79.8 | .36 | 10.7 | 90.5 |

HAc - Acetaldehyde
ACR - Acrolein
HOAc - Acetic Acid
AA - Acrylic Acid

Recycle Applications

Recycling of process streams is well known in the chemical process arts, and is usually implemented to formed following typical current commercial procedures using excess steam as the diluent. The feed consisted of 60.2% air, 7% propylene and 32.8% steam. The acrolein product stream of the first-stage reactor was directly introduced into the second-stage reactor for oxidation to acrylic acid, again following typical current commercial procedures. This experiment is presented in Table III.

Examples 9 and 10

These were performed under the conditions described in table III by the procedure of experiment B. However, the steam to the first-stage reactor was replaced by essentially dry nitrogen.

TABLE III

| OVER-ALL TWO-STAGE PERFORMANCE | | | |
|---|---|---|---|
| | Exp. | Example | |
| | B | 9 | 10 |
| CHC (Cal/(g-mole)(°C.) | 7.9 | 7.5 | 7.5 |
| SV | 1200 | 1200 | 1600 |
| $T_1$ | 334 | 322 | 330 |
| Mole % $C_3H_6$ Conv. | 96.1 | 96.5 | 95.2 |
| $T_2$ | 284 | 279 | 302 |
| Mole % ACR Conv. | 100 | 98.1 | 100 |
| 1st Stage Feed Water, m % | 32.8 | 0 | 0 |
| 2nd Stage Feed Water, m % | 39.5 | 5.3 | 5.7 |

ACR - Acrolein
SV - Space velocity
$T_1$ - First-stage reactor bath temperature, °C.
$T_2$ - Second-stage reactor bath temperature, °C.

The data reported in Table III compares the results of Experiment B (i) with that of Example 9, in which temperature of the second-stage reactor was essentially the same and (ii) with that of Example 10, in which the temperature of the second-stage reactor was raised about 18° C. As shown by the data the current conventional procedure (Experiment B conditions) has an acrolein conversion of 100 mole percent. In the essential absence of steam in the second-stage (Example 9) conversion in the second-stage drops (this does not affect first-stage performance by the process of this invention) to about 98 mole percent. Increasing the second-stage reactor temperature by about 18° C. (Example 10) restored the conversion to 100 mole percent. This was completely unexpected and could not be predicted.

What is claimed for:

1. In a process for producing acrylic acid by a two-stage catalytic oxidation of propylene, wherein the first stage reaction produces primarily acrolein and the second stage reaction produces primarily acrylic acid by oxidation of acrolein, said process optionally using one or more recycle streams to either or both stages, both stages operating on feed streams containing oxygen and added inert diluent gas, the improvement comprising (a) utilizing one or more essentially inert essentially anhydrous diluent gases free of any intentionally-added water in a mole ratio of about 2.0 to about 32.0 moles of diluent per mole of propylene as the essentially inert essentially anhydrous diluent gas feed added to the first stage, said added essentially inert essentially anhydrous diluent gas feed having a composite heat capacity of at least 7.95 calories/gram-mole (°C.) and an oxygen-containing stream containing from about 1.1 to about 2.1 moles of molecular oxygen per mole of propylene and (b) utilizing one or more essentially inert essentially anhydrous diluent gases free of any intentionally added water as the inert diluent gas feed to the second stage, said added essentially inert anhydrous diluent having a composite heat capacity of at least about 7.95 calories/gram-mole (°C.)

2. A process as claimed in claim 1 wherein the composite heat capacity of the essentially inert anhydrous diluent gas to the first stage is about 8 to about 20.

3. A process as claimed in claim 2 wherein the composite heat capacity of the essentially inert essentially anhydrous diluent gas to the first stage is about 10 to about 17.

4. A process as claimed in claim 1 wherein the water content of said essentially anhydrous diluent gas to the first stage is less than about 0.3 mole per mole of propylene.

5. A process as claimed in claim 1 wherein the oxygen is from a pure oxygen source.

6. A process as claimed in claim 1 wherein the essentially inert essentially anhydrous diluent gas comprises a recycled process stream from an acrolein recovery operation.

7. A process as claimed in claim 1 wherein the essentially inert essentially anhydrous diluent gas comprises a recycled process stream from an acrylic acid recovery operation.

8. In a process for producing acrylic acid by a two-stage catalytic oxidation of propylene, wherein the first-stage reaction produces primarily acrolein and the second-stage reaction produces primarily acrylic acid by oxidation of acrolein, said process utilizing one or more recycle streams to either or both stages, both stages operating on feed streams containing oxygen and an inert diluent gas, the improvement comprising (a) utilizing one or more essentially inert essentially anhydrous diluent gases free of any intentionally added water in a mole ratio of about 2.0 to about 32.0 moles of diluent per mole of propylene as the essentially inert essentially anhydrous diluent gas to the first-stage, said added essentially inert anhydrous diluent gas feed having a composite heat capacity of at least 7.95 calories/gram-mole (°C.) and an oxygen-containing stream containing from about 1.1 to about 2.1 moles of molecular oxygen per mole of propylene, (b) utilizing one or more essentially inert anhydrous diluent gases as the essentially inert essentially anhydrous diluent gas free of any intentionally added water to the second-stage gas comprising one or more inert essentially anhydrous diluent gases having a composite heat capacity of at least 7.95 calories/gram-mole (°C.), and (c) increasing the operating temperature of the second-stage about 5°-10° C. above that required if steam were present in the inlet stream to the second-stage at a concentration of about 45 mole percent of the inlet stream to the second-stage.

9. A process as claimed in claim 8 wherein the composite heat capacity of the essentially inert essentially anhydrous diluent gas to the first stage is about 8 to about 20.

10. A process as claimed in claim 9 wherein the composite heat capacity of the essentially inert essentially anhydrous diluent gas to the first stage is about 10 to about 17.

11. A process as claimed in claim 8 wherein the steam content of the diluent gas to the first stage is less than about 0.3 mole per mole of propylene.

12. A process as claimed in claim 8 wherein the oxygen is from a pure oxygen source.

13. A process as claimed in claim 8 wherein the essentially inert essentially anhydrous diluent gas comprises a recycled process stream from an acrolein recovery operation.

14. A process as claimed in claim 8 wherein the essentially inert essentially anhydrous diluent gas comprises a recycled process stream from an acrylic acid recovery operation.

15. In a process for producing acrylic acid by a two-stage catalytic oxidation of propylene, wherein the first-stage reaction produces primarily acrolein and the second-stage reaction produces primarily acrylic acid by oxidation of acrolein, said process utilizing one or more recycle streams to either or both stages, both stages operating on feed streams containing oxygen and an inert diluent gas, the improvement comprising (a) utilizing one or more essentially anhydrous diluent gases as the essentially inert essentially anhydrous diluent gas free of any intentionally added water in a mole ratio of about 2.0 to about 32.0 moles of diluent per mole of propylene to the first-stage, said added essentially inert essentially anhydrous diluent gas feed having a composite heat capacity of at least 7.95 calories/gram-mole (°C.) and an oxygen-containing stream containing from about 1.1 to about 2.1 moles of molecular oxygen per mole of propylene, (b) utilizing one or more essentially inert essentially anhydrous diluent gases free of any intentionally added water as the diluent gas to the second-stage, said added essentially inert anhydrous diluent gas feed having a composite heat capacity of at least 7.95 calories/gram-mole (°C.), and (c) increasing the available surface area of the second-stage catalyst sufficiently to compensate for any loss of catalyst efficiency caused by reduction or elimination of steam in the inlet stream to the second-stage.

16. A process as claimed in claim 15 wherein the composite heat capacity of the essentially inert essentially anhydrous diluent gas to the first-stage is about 8 to about 20.

17. A process as claimed in claim 16 wherein the composite heat capacity of the essentially inert essentially anhydrous diluent gas to the first-stage is about 10 to about 17.

18. A process as claimed in claim 15 wherein the steam content of the essentially inert essentially anhydrous diluent gas to the first-stage is less than about 0.3 mole per mole of propylene.

19. A process as claimed in claim 15 wherein the oxygen is from a pure oxygen source.

20. A process as claimed in claim 15 wherein the essentially inert essentially anhydrous diluent gas comprises a recycled process stream from an acrolein recovery operation.

21. A process as claimed in claim 18 wherein the essentially inert essentially anhydrous diluent gas comprises a recycled process stream from an acrylic acid recovery operation.

* * * * *